United States Patent
Chen

[11] Patent Number: 5,849,028
[45] Date of Patent: Dec. 15, 1998

[54] CATHETER AND METHOD FOR RADIOFREQUENCY ABLATION OF CARDIAC TISSUE

[75] Inventor: Peter Cheng Chen, Irvine, Calif.

[73] Assignee: Irvine Biomedical, Inc., Irvine, Calif.

[21] Appl. No.: 858,053

[22] Filed: May 16, 1997

[51] Int. Cl.⁶ .................................................. A61B 17/36
[52] U.S. Cl. .............................. 607/102; 606/41; 606/45; 607/101
[58] Field of Search .................................. 606/30, 31, 41, 606/42, 45–50; 607/101, 102, 122; 600/374

[56] References Cited

U.S. PATENT DOCUMENTS

| | | | |
|---|---|---|---|
| 5,398,683 | 3/1995 | Edwards et al. | 607/122 |
| 5,456,682 | 10/1995 | Edwards et al. | 606/31 |
| 5,500,012 | 3/1996 | Brucker et al. | 607/122 |
| 5,573,533 | 11/1996 | Strul | 606/34 |
| 5,582,609 | 12/1996 | Swanson et al. | 606/45 |
| 5,642,736 | 7/1997 | Avitall | 607/122 |

*Primary Examiner*—Michael Peffley

[57] ABSTRACT

An electrophysiology catheter suitable for radiofrequency ablation of cardiac tissue comprises an elongate catheter shaft wherein a distal tip section having multiple long electrodes and multiple temperature sensors in the proximity of the tissue contact sites and further comprising a close-loop temperature control mechanism for each electrode with at least a temperature sensor on an adjacent tiny ring.

18 Claims, 3 Drawing Sheets

5,849,028

CATHETER AND METHOD FOR RADIOFREQUENCY ABLATION OF CARDIAC TISSUE

FIELD OF THE INVENTION

The present invention generally relates to improved constructions for cardiovascular ablation catheters. More particularly, this invention relates to methods and apparatus for treating cardiac arrhythmias via a cardiovascular catheter having at least one temperature sensor in the proximity of the tissue contact site, while not in contact with any electrode, to acquire real-time temperature reading in conjunction with a control mechanism for ablating cardiac tissues.

BACKGROUND OF THE INVENTION

Symptoms of abnormal heart rhythms are generally referred to as cardiac arrhythmias, with an abnormally rapid heart beat being referred to as tachycardia. The present invention is concerned with the treatment of tachycardias which are frequently caused by the presence of an "arrhythmogenic site" or "accessory atrioventricular pathway" close to the surface of the upper chambers of a heart. The heart includes a number of normal pathways which are responsible for the propagation of electrical signals from upper to lower chamber necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the cardiac tissue.

Of particular interest to the present invention are radiofrequency (RF) ablation protocols which have proven to be highly effective in tachycardia treatment while exposing a patient to minimal side effects and risks. Catheter based radiofrequency ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal conducted signal patterns responsible for the tachycardia can be eliminated. However, in the case of atrial fibrillation (AFib), multiple arrhythmogenic sites and/or multiple accessory pathways exist. It becomes essential that true real-time temperature readings be obtained at the tissue contact sites for each and every ablating electrode to ensure appropriate energy control resulting in optimal desired lesions.

Atrial Fibrillation is believed to be the result of aberrant conduction of electrical signals within the atria, resulting in a condition in which the transmission of electrical activity becomes so disorganized that the atria contracts quiveringly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

Multiple arrhythmogenic sites and/or multiple accessory pathways exist in both endocardial and epicardial routes. For an epicardial approach, a catheter utilized in the radiofrequency ablation is inserted through a small surgery hole at the chest and is penetrated through the pericardium of the heart. The tip section of a catheter is referred to here as the portion of that catheter shaft containing the electrodes, which is either a fixed curve or a deflectable one. The catheter is then guided into epicardial surface of the heart by appropriate manipulation from the proximal end of the catheter.

The tip of a catheter must be manipulatable by a physician from the proximal end of the catheter, so that the electrodes at the tip section can be positioned against the tissue site to be ablated. The catheter must permit user manipulation of the tip even when the catheter shaft is in a curved and twisted configuration. The tip section of a conventional electrophysiology catheter that is deflectable usually contains one large electrode for ablation purpose. A temperature sensor is usually attached on that electrode. The securing point of the temperature sensor on the electrode is usually on the opposite side of the tissue contact point to avoid temperature surge when the RF energy is suddenly delivered. And the measured temperature from said sensor does not reflect the true real-time temperature at the tissue contact point for temperature control purpose. It has been a fact that too high an ablation temperature might cause tissue charring or tamponade. It is useless when the measured temperature does not reflect the true temperature.

While radiofrequency electrophysiology ablation procedures using an existing catheter design has produced some promising results, the tip section of a known catheter usually have one large electrode for ablation purpose. The temperature sensor is usually secured at the opposite side of the tissue contact site. The measured temperature may not be the true temperature because of the location of the temperature sensor on the electrode; wherein the RF energy delivered to the tissue also conductively transfers to the temperature sensor. Therefore, the measured temperature reflects the energy from the electrode rather than from the surrounding tissue. During ablation procedures, once the measured temperature which may be artificially higher than the real tissue temperature, exceeds the pre-patent determined safety limit, the energy source is cut off even the tissue temperature is still relatively low.

It is the purpose of this invention to provide an ablation catheter having temperature sensor secured adjacent to the electrode, while not in contact with any electrode, to independently and accurately control the energy delivery to each electrode; wherein the temperature sensor is secured to the proximity of the tissue contact site. The temperature set-point and power set-point can be controlled for effectively treating the AFib.

SUMMARY OF THE INVENTION

The present invention provides an improved ablation catheter which can be used in ablating the multiple arrhythmogenic points of a patient. This catheter is particularly useful for treating the patients with atrial fibrillation (AFib) syndrome. In one embodiment, an ablation catheter comprises a catheter shaft having a distal section, a distal end, a proximal end, and at least a lumen extending therebetween, wherein the distal tip section has a plurality of long electrodes and a plurality of tiny non-electrode metallic rings adjacent to the electrodes, for securing the temperature sensors; a handle secured at the proximal end of the catheter shaft; and at least one temperature sensor associated, but not in contact, with each electrode.

The multiple temperature sensors are important to independently measure and monitor the true tissue contact temperature, but not the electrode temperature itself, during RF energy delivery. During multiple electrodes ablation, the tissue contact temperatures at various locations may be different as a function of the RF energy delivery time, the intimacy of tissue-electrode contact, the location of the temperature sensor relative to the electrode, and the surrounding blood flow pattern. Due to continuous heart movement, a good tissue contact becomes significant in affecting the temperature readings. The size of lesion may be a function of RF energy, time, tissue contact characteristics, and temperature control.

A pair of wires is connected to a temperature sensor located on a tiny ring adjacent to an electrode. Typically, the temperature sensor is a thermocouple consisting of a pair of dissimilar metals, usually copper and constantan which forms a T-type thermocouple. The thermocouple wires are also connected to a radiofrequency generator through the connector and cable so that they will be connected and disconnected as the catheter is plugged and unplugged.

In another embodiment, an ablation catheter further comprises a close-loop temperature control mechanism for each electrode having at least a temperature sensor on an adjacent tiny ring. An ablation catheter of this invention further comprises RF energy delivery. To better control the desired lesion, more RF energy may be needed when the measured tissue contact temperature is relatively low. On the other hand, less RF energy is needed when a relatively high tissue contact temperature is detected. In still another embodiment, an ablation catheter further comprises a programmed temperature control mechanism for independently and accurately controlling each electrode ablation of the catheter system according to the software algorithm prepared by the operator.

In an alternate embodiment, an ablation catheter comprises the ablating electrodes of longer than 2 mm in length, preferably 4 to 10 mm. The electrode diameter is usually between 7 and 9 French. The temperature sensor is usually a thermocouple means or a thermistor means. The tiny ring where a temperature sensor is secured, is about 0.2 mm in length or less and is located next to an electrode with a spacing from that electrode of about 0.2 mm or less. The tiny ring would pick up the temperature from the contact tissue rather than from the electrode. The material for electrodes and the tiny rings at the tip section may be consisted of a metal or their mixture such as platinum, iridium, gold, silver, stainless steel, and Nitinol.

In still another embodiment, the ablation catheter further comprises a steering mechanism on the handle. For an epicardial ablation, the inner side of the electrodes is to contact the tissue while the outer side of said electrode faces the pericardium, and is not involved in delivery of RF energy. The ablation catheter further comprises a plurality of deflectable curves on the distal tip section of the catheter shaft being provided by the steering mechanism on the handle. By providing a steerable ablation catheter with a plurality of deflectable curves, the catheter can fit the epicardial contours appropriately. The steering mechanism is well known to those who are skilled in the art.

A method for operating an ablation catheter having at least one long electrode and at least a temperature sensor secured at a tiny ring within a heart comprises: percutaneously introducing the distal end of the catheter through a blood vessel; approaching the catheter to the target chamber of the heart; positioning the catheter at the cardiac tissue of the heart, wherein the plurality of electrodes with at least one temperature sensor secured on a tiny non-electrode metallic ring adjacent to an electrode are disposed at the cardiac surface of the heart, and wherein the temperature sensor is attached to a tiny ring contacting the tissue; and applying radiofrequency energy to the target tissues through at least one of multiple electrodes with at least one temperature sensor on a tiny ring adjacent to said electrode.

In a further embodiment, a method for operating an ablation catheter further comprises a close-loop temperature control mechanism for each electrode having a temperature sensor on an adjacent tiny ring. In a still further embodiment, a method for operating an ablation catheter further comprises comprising a programmed temperature control mechanism for independently controlling the delivery of RF energy of each electrode of the ablation catheter.

The method and apparatus of the present invention have several significant advantages over known catheters or ablation techniques, particularly the temperature sensors in the proximity of the tissue contact site, but not in contact with any electrode and a close-loop temperature control mechanism independently for each electrode at the tip section.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
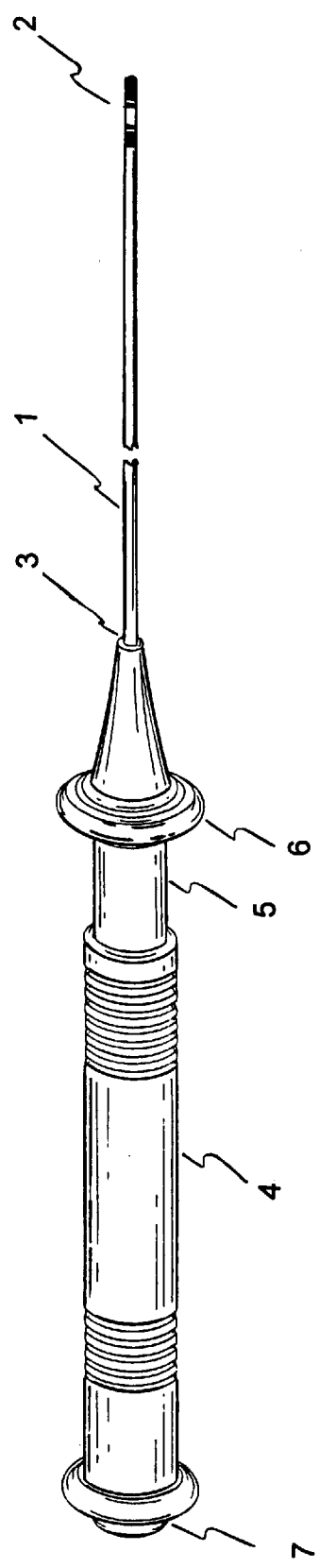
FIG. 1 is an overall view of an ablation catheter having multiple electrodes and multiple temperature sensors constructed in accordance with the principles of the present invention.

FIG. 1 shows an electrophysiology catheter constructed in accordance with the principles of the present invention comprising: a catheter shaft 1 having a distal tip section 2, a distal end, a proximal end 3 and a lumen extending therebetween. A handle 4 is attached to the proximal end of the catheter shaft 1. The tip section may be a fixed curve or deflectable by employing a steering mechanism 5 at the handle 4. A push-pull plunger 6 is employed to deflect the tip section 2 of the catheter shaft 1. A connector 7 is secured at the proximal end of the handle 4. At least one long electrode available for ablation use is disposed on the tip section 2. At least one tiny ring where a temperature sensor is secured onto, is disposed adjacent to and near an electrode.

Figure 2:
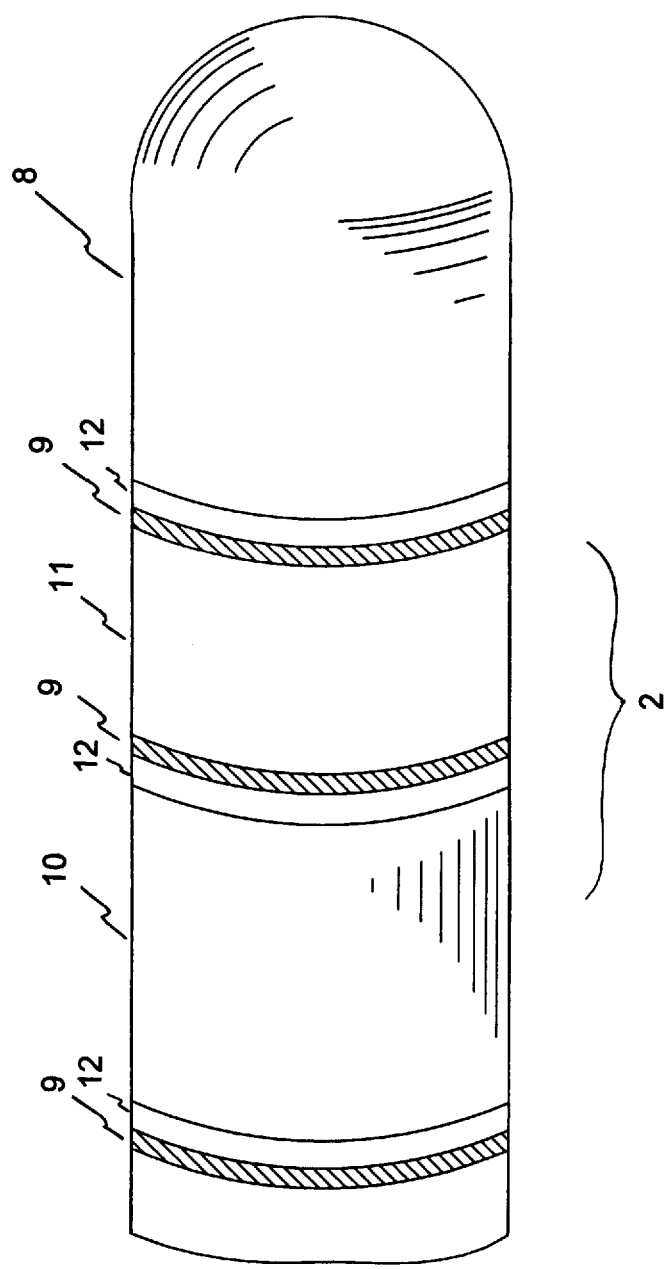
FIG. 2 is a perspective view of the distal section of the catheter of FIG. 1.

FIG. 2 shows a perspective view of the distal section of the catheter. The distal section 2 comprises a tip electrode 8 and at least one band electrode 10. A plurality of tiny non-electrode metallic rings 9 are disposed adjacent to the electrode 8 or 10. At least a temperature sensor, either a thermocouple means or a thermister means, is secured to the tiny ring 9 and is not in contact with any ablating electrode, to measure the tissue contact temperature when RF energy is delivered. The spacing material 11 between the tiny rings 9 and the spacing material 12 between a tiny non-electrode metallic ring and an electrode are not conductive.

Figure 3:
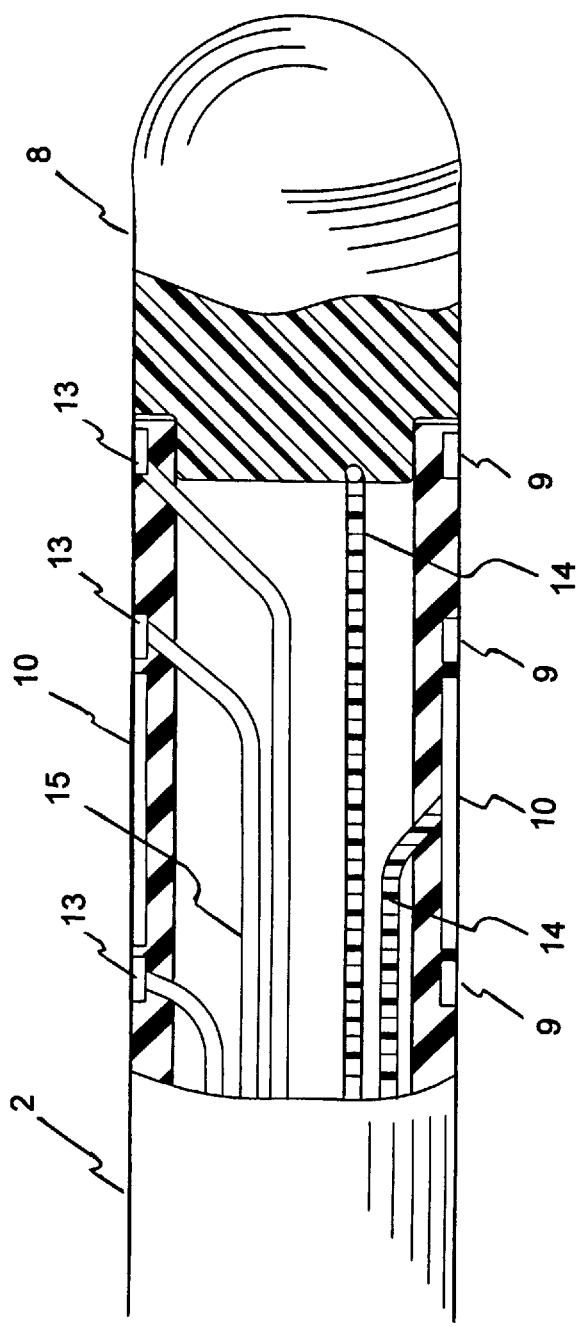
FIG. 3 is a cross sectional view of the distal section of the catheter.

FIG. 3 shows a cross sectional view of the tip section. A temperature sensor 13 is secured to the tiny non-electrode metallic ring 9 while a sensing wire 15 from the thermocouple or thermister is externally connected to a temperature measuring circuit inside the RF generator. The temperature reading is displayed and is also relayed to a close-loop temperature control mechanism to adjust the RF energy output. The RF energy delivered is thus controlled by the temperature sensor reading and by a pre-programmed temperature control algorithm.

A conducting wire 14 from each electrode 8 or 10 passes through the lumen of the catheter shaft and is connected to the connector 7 at the proximal end of said catheter. The conducting wire from the connector 7 is externally connected to an EKG monitor for monitoring cardiac electrical signals during electrophysiology mapping procedure or to an RF ablation generator during catheter ablation. Therefrom, the RF energy is transmitted through the wire to the individual electrode and is delivered to the target tissue.

From the foregoing, it should now be appreciated that an improved ablation electrophysiology catheter system having multiple temperature sensors which are positioned in the proximity of the tissue contact sites, but not in contact with any electrode, and a close-loop temperature control mechanism has been disclosed for cardiac ablation procedures. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An ablation catheter system comprising:
    a catheter shaft having a distal tip section, a distal end, a proximal end and at least one lumen extending therebetween, wherein the distal tip section has at least one long electrode and at least one non-electrode metallic ring electrically isolated from and located near the at least one long electrode;
    at least one temperature sensor is secured to the non-electrode metallic ring; and
    a handle attached to the proximal end of the catheter shaft.

2. The ablation catheter system as in claim 1, further comprising a programmed temperature control mechanism connected to the at least one temperature sensor and to the at least one long electrode for independently selecting and controlling energy delivery from an external RF generator to the long electrode.

3. The ablation catheter system of claim 1, further comprising a steering mechanism disposed on the handle to control the deflection of the distal tip section of the catheter shaft.

4. The ablation catheter system as in claim 3, wherein the steering mechanism provides a plurality of deflectable curves on the distal tip section of the catheter shaft.

5. The ablation catheter system as in claim 1, wherein the temperature sensor is a thermocouple means.

6. The ablation catheter system as in claim 1, wherein the temperature sensor is a thermistor means.

7. A method for operating an ablation catheter system within a heart, the catheter system comprising: a catheter shaft having a distal tip section, a distal end, a proximal end and at least one lumen extending therebetween, wherein the distal tip section has at least one long electrode and at least one non-electrode metallic ring electrically isolated from and located near the at least one long electrode; at least one temperature sensor is secured to the non-electrode metallic ring; and a handle attached to the proximal end of the catheter shaft;
    the method comprising the steps of:
        (a) percutaneously introducing the distal end of the catheter through a blood vessel to the heart;
        (b) positioning the tip section of the catheter inside the heart, wherein the at least one electrode having at least one temperature sensor secured on a non-electrode metallic ring is positioned at a surface of the heart; and
        (c) delivering radiofrequency energy from an external RF generator to the at least one long electrode.

8. The method for operating an ablation catheter system within a heart as in claim 7, the catheter system further comprising a programmed temperature control mechanism connected to the at least one temperature sensor and to the at least one long electrode for independently selecting and controlling energy delivery from an external RF generator to the long electrode.

9. The method for operating an ablation catheter system within a heart as in claim 7, the catheter system further comprising a steering mechanism disposed on the handle to control the deflection of the distal tip section.

10. The method for operating an ablation catheter system within a heart as in claim 9, wherein the steering mechanism of the catheter system provides a plurality of deflectable curves on the distal tip section of the catheter shaft.

11. The method for operating an ablation catheter system within a heart as in claim 7, wherein the temperature sensor of the catheter system is a thermocouple means.

12. The method for operating an ablation catheter system within a heart as in claim 7, wherein the temperature sensor of the catheter system is a thermistor means.

13. A cardiac tissue ablation method comprising: providing an ablation system comprising a catheter shaft having a distal tip section, a distal end, a proximal end and at least one lumen extending therebetween, wherein the distal tip section has at least one long electrode and at least one non-electrode metallic ring electrically isolated from and located near the at least one long electrode, at least one temperature sensor is secured to the non-electrode metallic ring; a handle attached to the proximal end of the catheter shaft; and applying radiofrequency energy to the tissue through the at least one long electrode having the at least one temperature sensor on a non-electrode metallic ring.

14. The cardiac tissue ablation method providing an ablation catheter as in claim 13, the ablation catheter further comprising a programmed temperature control mechanism connected to the at least one temperature sensor and to the at least one long electrode for independently selecting and control energy delivery from an external RF generator to the long electrode.

15. The cardiac tissue ablation method providing an ablation catheter as in claim 13, the ablation catheter further comprising a steering mechanism disposed on the handle to control the deflection of the distal tip section.

16. The cardiac tissue ablation method providing an ablation catheter as in claim 15, wherein the steering mechanism of the ablation catheter provides a plurality of deflectable curves on the distal tip section of the catheter shaft.

17. The cardiac tissue ablation method providing an ablation catheter as in claim 13, wherein the temperature sensor of the ablation catheter is a thermocouple means.

18. The cardiac tissue ablation method providing an ablation catheter as in claim 13, wherein the temperature sensor of the ablation catheter is a thermistor means.

* * * * *